(12) United States Patent
De La Prieta et al.

(10) Patent No.: US 7,270,888 B2
(45) Date of Patent: Sep. 18, 2007

(54) COMPOSITE BODY MADE OF CERAMIC LAYERS AND METHOD FOR ITS MANUFACTURE

(75) Inventors: Claudio De La Prieta, Stuttgart (DE); Thomas Schulte, Stuttgart (DE); Erhard Hirth, Ellhofen (DE); Annika Kristoffersson, Hisings Backa (SE); Stefan Nufer, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/514,333

(22) PCT Filed: Aug. 25, 2003

(86) PCT No.: PCT/DE03/02829

§ 371 (c)(1),
(2), (4) Date: Nov. 11, 2004

(87) PCT Pub. No.: WO2004/020366

PCT Pub. Date: Mar. 11, 2004

(65) Prior Publication Data

US 2005/0175853 A1      Aug. 11, 2005

(30) Foreign Application Priority Data

Aug. 28, 2002   (DE) ................ 102 39 416

(51) Int. Cl.
*B32B 15/04*    (2006.01)
*B32B 9/00*     (2006.01)
*C04B 37/00*    (2006.01)

(52) U.S. Cl. .............. 428/469; 428/472; 428/701; 428/702; 156/89.11; 156/89.28; 156/155

(58) Field of Classification Search ............. None
See application file for complete search history.

(56) References Cited

U.S. PATENT DOCUMENTS

| | | | | |
|---|---|---|---|---|
| 3,277,150 A | * | 10/1966 | Berry et al. ............. | 228/121 |
| 5,776,620 A | | 7/1998 | Alperine et al. | |
| 5,985,464 A | | 11/1999 | Nechansky et al. | |
| 2004/0129370 A1 | * | 7/2004 | Taylor et al. .......... | 156/89.11 |

FOREIGN PATENT DOCUMENTS

| | | |
|---|---|---|
| DE | 4 018 715 | 12/1991 |
| EP | 0 380 200 | 8/1990 |
| EP | 0 726 238 | 8/1996 |
| GB | 976 660 | 12/1964 |
| GB | 1 259 633 | 1/1972 |
| WO | 02 100798 | 12/2002 |

* cited by examiner

*Primary Examiner*—Jennifer McNeil
*Assistant Examiner*—Timothy M. Speer
(74) *Attorney, Agent, or Firm*—Kenyon & Kenyon LLP

(57) ABSTRACT

A composite body made of at least two ceramic layers, in which the ceramic layers are permanently bonded to one another at defined bonding points by a contact layer made of a bonding material. To achieve a permanent, thermally stable bond of ceramic layers having different coefficients of thermal expansion, the bonding material has a low modulus of elasticity. During the manufacture of the composite body, the bonding points of the ceramic layers are pretreated to form a porous surface structure, the bonding material is applied to these bonding points, and after the ceramic layers are laid one on top of another with bonding points facing toward one another and bonding material lying between them, the assembled composite body is subjected to a heat treatment.

11 Claims, 1 Drawing Sheet

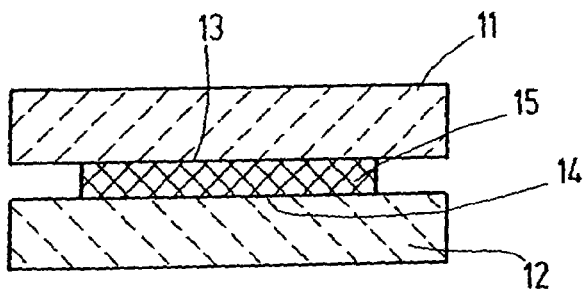
Fig.1
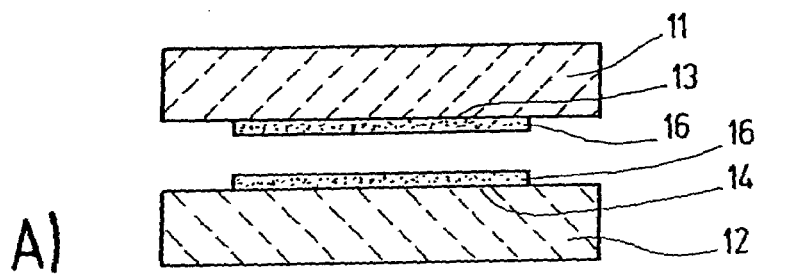
A)
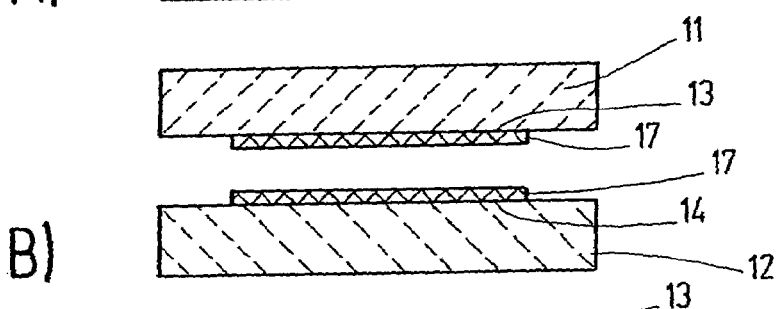
B)
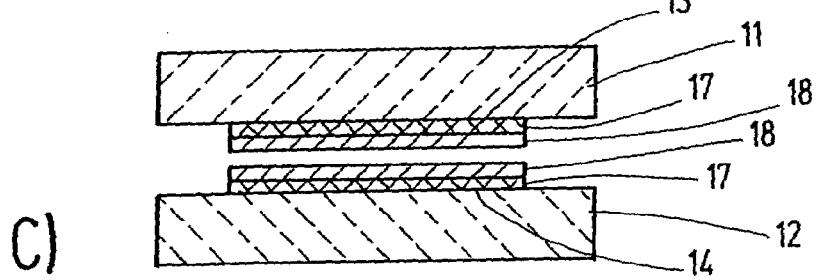
C)
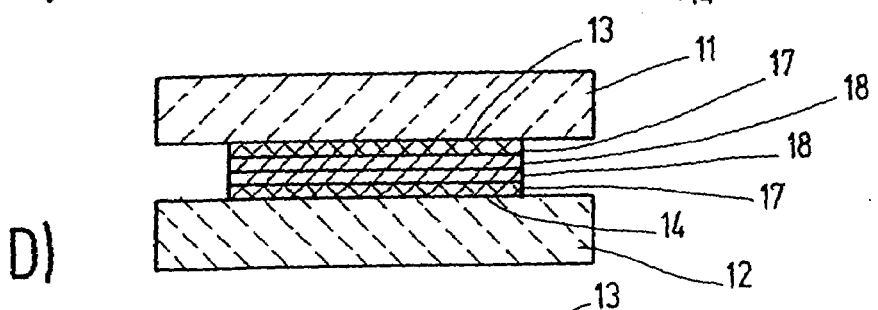
D)
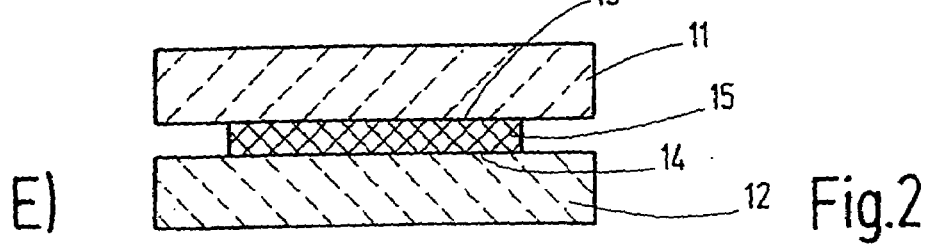
E)  Fig.2

COMPOSITE BODY MADE OF CERAMIC LAYERS AND METHOD FOR ITS MANUFACTURE

FIELD OF THE INVENTION

The present invention is directed to a composite body made of at least two ceramic layers, and a method for its manufacture.

BACKGROUND INFORMATION

In a composite body made of two non-metal or two metal elements or one non-metal element and one metal element (German patent document no. 197 04 357), the bonding material is made of metal, e.g., Al, Cu, Zn, Mg, Ag, Au, Si, Fe, Ti, Ge, Sn, or the like, or an alloy made of these metals. The bonding material is introduced through a casting process, e.g., diecasting or infiltration. For this purpose, the two elements are placed tightly and directly against one another or on top of one another and are encapsulated. The liquefied bonding material is able to migrate between the two elements because of the fine surface roughness which they always have and therefore permanently bond the two elements to one another. In order to increase the quantity of bonding material penetrating between the two elements, one or even both of the surfaces of the adjoining elements facing toward one another is roughened. This roughening may be performed through simple grinding or by implementing groove-shaped channels.

SUMMARY OF THE INVENTION

The composite body according to the present invention having the features of claim 1 has the advantage that due to the low modulus of elasticity, the bonding material is ductile and bonds the ceramic layers to one another permanently and stably, even if they have greatly differing temperature coefficients, as is the case if the composite body is constructed from zirconium oxide and aluminum oxide layers, for example. The ductile bonding material compensates for the thermal expansion of the ceramic layers at the boundary surfaces through elastic-plastic deformation and thus reduces the mechanical stress which arises at higher temperatures, which lie between 700° C. and 1000° C., when the composite body is used for a sensor element of a lambda probe, for example. The reduction of the thermal stress between the ceramic layers results in a higher aging resistance of the sensor element. The bonding points between the ceramic layers have a high density, so that bushings through the ceramic layers may be implemented with higher gas-tightness.

Advantageous refinements to and improvements on the composite body are described herein.

According to an exemplary embodiment of the present invention, the two ceramic layers have a porous surface structure at their bonding points. Through this porous surface structure, an optimum mechanical bond of bonding material and ceramic is ensured, since the porous layer is wetted well by the melt of the bonding material and teeth are thus produced when the bonding material cools. The teeth are also the reason for the high gas-tightness of the bond between the ceramic layers.

According to exemplary embodiments of the present invention, metals having a high melting point, e.g., boron (B), chromium (Cr), nickel (Ni), platinum (Pt), titanium (Ti), or alloys of these metals are used as starting materials for the bonding material. However, reactive metal-ceramic mixtures are also used as the bonding material. For example, on the one hand, magnesium oxide, aluminum oxide, or spinel and, on the other hand, aluminum or aluminum-magnesium alloys react with one another. In the latter case of the embodiment of the bonding material, good bonding is achieved both on a ceramic layer made of aluminum oxide, for example, and on a ceramic layer made of zirconium oxide, for example, so that the additional production of porosity in the surfaces of these ceramic layers may be dispensed with.

In an exemplary method for manufacturing the composite body according to the present invention using a post-firing process, a porous surface structure is first produced on the bonding points of the ceramic layers, which may be by applying a layer made of a paste having pore-forming components using the screen print or the dispensing method and subsequent, separate heat treatment of the ceramic layers. During the heat treatment, the pore-forming components evaporate and the porous surface structure is produced on the bonding points. The bonding material is then applied to the porous surface structure of the sintered ceramic layers, which may be in the screen print or dispensing method, the two ceramic layers are laid one on top of another together with bonding points facing toward one another and bonding material lying between them to form the composite body, and the composite body is subjected to a heat treatment (post-firing). This method has the advantage that through the separate heat treatment (sintering) of the ceramic layers before the assembly into the composite body, the sintering parameters may be selected freely and the porous additional layers may be manufactured using any arbitrary pore-forming materials.

In an alternative method, the formation of a porous surface structure is prepared for on the bonding points of each ceramic layer by applying a layer made of a paste having pore-forming components using the screen print or the dispensing method. The bonding material is then immediately applied as a layer, which may again include using the screen print or the dispensing method, onto the paste layer on at least one, which may be on each, ceramic layer. To form the composite body, the coated ceramic layers are then laid one on top of another with bonding points facing toward one another and the bonding material lying between them, and the composite body is subjected to a heat treatment (co-firing). In this co-firing process, it is necessary for the ceramic layers to require uniform sintering parameters and—since the porous surface structure does not form until during the heat treatment—for the pore-forming materials in the paste to be selected in such a way that the pore formation starts before the beginning of the bonding process between the bonding material and paste material.

According to a further alternative method, the composite body may also be manufactured through reaction sintering. In this case, the porous additional layers, i.e., the application of the paste having pore-forming materials, are dispensed with and the bonding material is applied directly to the bonding points of the ceramic layers. After the ceramic layers are laid one on top of another together with bonding points facing toward one another and bonding material lying between them, the composite body is reaction sintered.

BRIEF DESCRIPTION OF THE DRAWINGS

FIG. 1 shows a cross-section of a composite body made of two ceramic layers.

FIG. 2 shows the composite body shown in FIG. 1 in different steps A-E of its manufacture.

DETAILED DESCRIPTION

The composite body sketched in the cross-section in FIG. 1 includes two ceramic layers 11, 12, which have different coefficients of thermal expansion. For example, the upper ceramic layer 11 is made of zirconium oxide ($ZrO_2$) and the lower ceramic layer is made of aluminum oxide ($Al_2O_3$). Upper ceramic layer 11 has a thermal coefficient of expansion of approximately $10*10^{-6}/°K$, while in contrast ceramic layer 12 has a coefficient of expansion of approximately $8*10^{-6}/°K$. A flat bonding point 13 and 14 is defined on each ceramic layer 11 and 12, respectively, in whose region both ceramic layers 11, 12 are bonded to one another with high-temperature stability and thermomechanical stability by a contact layer 15 made of a bonding material. For this purpose, a bonding material which has a low modulus of elasticity is used. Starting materials for bonding material 15 are either metals having a high melting point or reactive metal-ceramic mixtures. Examples of metals having a high melting point are boron (B), chromium (Cr), nickel (Ni), platinum (Pt), and titanium (Ti). Alloys made of these metals may also be used as the bonding material. Reactive metal-ceramic mixtures are composed, for example, of magnesium oxide (MgO), aluminum oxide ($Al_2O_3$), or spinel, on the one hand, and aluminum or aluminum-magnesium alloys, on the other hand, which react with one another upon heat treatment (reaction sintering).

Because of the low modulus of elasticity, bonding material 15 is ductile and compensates, upon heating of the composite body to high temperatures, e.g., 700° C.-1000° C., for the differing expansions of both ceramic layers 11, 12 through elastic-plastic deformation, so that the mechanical stress between both ceramic layers 11, 12 is largely reduced. Through the good bonding of ceramic layers 11, 12 to the bonding material and through the filling of the pores in the surface structure of ceramic layers 11, 12 by the bonding material, a high material density arises at bonding points 13, 14, so that bushings through the composite body which lie in the area of bonding points 13, 14 may be implemented with high gas-tightness. In order to improve the bonding of contact layer 15 to both ceramic layers 11, 12 even further, ceramic layers 11, 12 are provided with a porous surface structure in the region of their bonding points 13, 14, into which the liquid bonding material of contact layer 15 penetrates and in which "teeth" form after solidification.

In FIG. 2, different manufacturing steps A-E of the composite body during its manufacture are illustrated. Accordingly, the method for manufacturing the composite body runs as follows:

First, a porous surface structure is manufactured on each of bonding points 13, 14 on ceramic layers 11, 12. For this purpose, a layer 16 made of a paste containing a pore-forming material is applied to each of boundary layers 13, 14 using screen print, spray, or dispensing methods (FIG. 2A). For example, flame soot is used as the pore-forming material. Ceramic layers 11, 12 are subjected separately to a heat treatment in a sintering process. The flame soot is combusted during this sintering process and a porous layer 17 arises on bonding points 13, 14 (FIG. 2B). The bonding material is now applied in the form of a layer 18 onto each of porous layers 17 (FIG. 2C). The application is again performed using the screen print or the dispensing method. Subsequently, ceramic layers 11, 12 provided with layers 18 are laid one on top of another together with bonding points 13, 14 facing toward one another to form the composite body in such a way that layers 18 are in contact (FIG. 2D). The composite body thus assembled is subjected to a heat treatment, i.e., a post-firing process. At the same time, the molten bonding material infiltrates into porous layer 17 and solid contact layer 15 forms between bonding points 13, 14 after cooling (FIG. 2E).

In an alteration of the manufacturing method, ceramic layers 11, 12, which are provided in their bonding points 13, 14 with layers 16 made of a paste having pore-forming components, are not subjected to a separate sintering process, but rather the porous surface structure of bonding points 13, 14 is first manufactured in the assembled composite body, which is subjected to a co-firing. In this case, immediately after layers 16 made of ceramic paste are applied, layers 18 made of bonding material are applied to layers 16. The application is again performed using the screen print or the dispensing method. Then, to form the composite body, coated ceramic layers 11, 12 are laid one on top of another together with bonding points 13, 14 facing toward one another and layers 16, 18 lying between them, and the composite body thus assembled is subjected to a heat treatment (sintering). The composition of the ceramic pastes in layers 16 is adjusted in such a way that during the heat treatment of the composite body, e.g., in the heating phase during sintering, the pores are first formed in layers 16 in that, for example, the flame soot from the ceramic paste combusts, and subsequently the molten bonding material from layer 18 penetrates (infiltrates) into the pores which are forming.

If metallic material is not used as the bonding material, but rather a metal-ceramic mixture, the separate method step of applying layer 16 made of ceramic paste having pore-forming components to produce a porous layer 17 on bonding points 13, 14 between ceramic layers 11, 12 may be dispensed with. Through the reactive bonding material, in reaction sintering, good bonding is achieved both on ceramic layer 11 made of zirconium oxide and also on ceramic layer 12 made of aluminum oxide.

The exemplary embodiment and/or exemplary method of the present invention is not restricted to the exemplary embodiment described. Thus, the composite body may contain more than two ceramic layers 11, 12, a contact layer 15 always' being produced between two ceramic layers for a permanent, thermally stable bond between the ceramic layers.

A field of use of the composite body described is the manufacture of a sensor element for a lambda probe. Ceramic layers 11, 12, between which functional layers, such as pump cells, Nernst cells, and resistance heaters, are then also embedded, are implemented as ceramic films. The ceramic films which have not yet been subjected to a sintering process are referred to as green films, which are provided at bonding points 13, 14 with layers made of ceramic paste and bonding material in the same way as described above.

What is claimed is:

1. A composite body comprising:
  a contact layer; and
  at least two ceramic layers, which are bonded to one another permanently at defined bonding points by the contact layer, wherein the contact layer is made of a bonding material which has a modulus of elasticity sufficiently low so as to allow it to compensate for differing expansions of the at least two ceramic layers, and wherein the at least two ceramic layers have a porous surface structure at their bonding points and the bonding material is infiltrated into pores of the porous surface structure of each of the at least two ceramic layers.

2. The composite body of claim 1, wherein the ceramic layers have different coefficients of thermal expansion.

3. The composite body of claim 1, wherein one of the ceramic layers is made of zirconium oxide and another of the ceramic layers is made of aluminum oxide.

4. The composite body of claim 1, wherein the bonding material contains metals having a high melting point.

5. The composite body of claim 1, wherein the bonding material is a reactive metal-ceramic mixture.

6. A method for manufacturing a composite body, the method comprising:
  pretreating bonding points of at least two ceramic layers to form a porous surface structure;
  applying bonding material to the pretreated bonding points of at least one of the ceramic layers;
  laying the ceramic layers one on top of another, wherein the bonding points face toward one another and the bonding material is lying between them to form the composite body; and
  subjecting the composite body to a heat treatment such that molten bonding material infiltrates into pores of the porous surface structure of each of the at least two ceramic layers;
  wherein the composite body includes a contact layer, and the at least two ceramic layers, which are bonded to one another permanently at the bonding points by the contact layer, and wherein the contact layer is made of the bonding material which has a modulus of elasticity sufficiently low so as to allow it to compensate for differing expansions of the ceramic layers.

7. The method of claim 6, wherein a layer made of a ceramic paste having pore-forming components is applied to the bonding points to form the porous surface structure.

8. The method of claim 7, wherein the ceramic paste is applied using one of a screen print process, a spray process, and dispensing process.

9. The method of claim 7, wherein the ceramic layers provided with the layers made of ceramic paste are subjected to a heat treatment before applying the bonding material.

10. The method of claim 6, wherein the bonding material is applied using one of a screen print process and a dispensing process.

11. The method of claim 6, wherein the applying of the bonding material to the pretreated bonding points includes each of the at least two ceramic layers.

* * * * *